United States Patent

Ferrati

[11] Patent Number: 5,961,541
[45] Date of Patent: Oct. 5, 1999

[54] ORTHOPEDIC APPARATUS FOR WALKING AND REHABILITATING DISABLED PERSONS INCLUDING TETRAPLEGIC PERSONS AND FOR FACILITATING AND STIMULATING THE REVIVAL OF COMATOSE PATIENTS THROUGH THE USE OF ELECTRONIC AND VIRTUAL REALITY UNITS

[76] Inventor: Benito Ferrati, Via della Polveriera N.41, 20026 Novate Milanese Milan, Italy

[21] Appl. No.: 09/149,131

[22] Filed: Sep. 8, 1998

Related U.S. Application Data

[63] Continuation-in-part of application No. 08/764,018, Dec. 11, 1996, abandoned.

[30] Foreign Application Priority Data

Jan. 2, 1996 [IT] Italy .................................. MI96A0001
Oct. 27, 1997 [EP] European Pat. Off. ............... 97830547

[51] Int. Cl.$^6$ .............................. G09B 3/00; A63B 24/00
[52] U.S. Cl. ................................ 607/49; 482/4; 482/902; 482/66; 434/307 R
[58] Field of Search .......................... 602/23, 26; 607/48, 607/49; 434/255, 307 R; 482/4, 902, 66; 601/34, 35

[56] References Cited

U.S. PATENT DOCUMENTS

| | | |
|---|---|---|
| 4,256,098 | 3/1981 | Swan et al. . |
| 4,499,900 | 2/1985 | Petrofsky . |
| 4,557,257 | 12/1985 | Fernandez et al. . |
| 4,760,850 | 8/1988 | Phillips . |
| 5,282,460 | 2/1994 | Boldt . |
| 5,476,441 | 12/1995 | Durfee . |
| 5,490,784 | 2/1996 | Carmein . |
| 5,562,572 | 10/1996 | Carmein . |
| 5,577,981 | 11/1996 | Jarvik . |
| 5,580,249 | 12/1996 | Jacobson . |
| 5,656,904 | 8/1997 | Lander ............................... 318/568.12 |

FOREIGN PATENT DOCUMENTS

| | | |
|---|---|---|
| 0 667 603 A1 | 8/1995 | European Pat. Off. . |
| 295 11 509 | 7/1995 | Germany . |
| 1 153 225 | 10/1982 | Italy . |
| 1 178 548 | 10/1984 | Italy . |
| 20882 A/90 | 7/1990 | Italy . |
| WO89/01353 | 8/1988 | WIPO . |

OTHER PUBLICATIONS

McNeely, "Robotic Graphics: A New Approach to Force Feedback for Virtual Reality", IEEE (1993).

Stevens, "Flights Into Virtual Reality", Science Psychology, The Washington Post (Mar. 27, 1995).

*Primary Examiner*—Richard J. Apley
*Assistant Examiner*—William LaMarca
*Attorney, Agent, or Firm*—Wenderoth, Lind & Ponack, L.L.P.

[57] ABSTRACT

An exoskeleton for the support of a patient's body is jointed opposite the hip and knee articulations, and is provided with a number of small actuators that are designed to move jointed parts of the exoskeleton in accordance with the human gait. A control unit is programmed to control the operation of the actuators so as to impress on the exoskeleton the movements of the human gait. A remote control for operation of the control unit allows the patient to transmit commands to the unit in order to start or stop the lower limbs, as well as to adjust the step speed. An electronic virtual reality unit transmits to the patient, through a special helmet, virtual reality pictures and stimulation interactive with the walking movement that is impressed by the exoskeleton on the patient's body. A framework can be used to steady and support the person and allow the person to walk at the same time, and has grips having operating push buttons for the remote control unit. Alternatively, a rail is suspended at a distance from the ground higher than human height for supporting and guiding a ball bearing or a slide slidable inside or on the rail. A metal framework is supported by the ball bearing or slide and provided with two suspenders or rods for supporting the exoskeleton of the patient.

41 Claims, 5 Drawing Sheets

ORTHOPEDIC APPARATUS FOR WALKING AND REHABILITATING DISABLED PERSONS INCLUDING TETRAPLEGIC PERSONS AND FOR FACILITATING AND STIMULATING THE REVIVAL OF COMATOSE PATIENTS THROUGH THE USE OF ELECTRONIC AND VIRTUAL REALITY UNITS

This application is a continuation in part of application Ser. No. 08/764,018, filed Dec. 11, 1996, now abandoned.

BACKGROUND OF THE INVENTION

1. Field of the Invention

The present invention relates to an orthopedic apparatus for walking and rehabilitating disabled persons including tetraplegic persons and for facilitating and stimulating the revival of comatose patients.

2. State of the Prior Art

Orthopedic apparatus have been conceived for rehabilitating persons that are disabled in the motor abilities of their lower limbs (paraplegics, etc.) which are designed to allow walking for the purpose not only of improving the muscle, nerve and bone tonus, but also, and mainly, to stimulate and aid in the recovery of their motor ability.

Known orthopedic apparatus that are designed to stimulate and exercise the movement of the lower limbs and to allow walking, that have been designed by the present inventor include those disclosed in Italian patents 1,153,225, filed Oct. 12, 1982 and 1,178,548, filed Oct. 3, 1984, as well as Italian patent application 20,882 A/90 filed Jul. 9, 1990.

Of particular interest is the orthopedic apparatus described in Italian patent 1,178,548. This apparatus has the aim of allowing persons who have serious injuries to their motor abilities of their lower limbs to walk. The apparatus consists of a semi-rigid apparatus or exoskeleton that supports the bust and the lower limbs. It is jointed opposite the hip and knee articulations, and is equipped with small actuators (microcylinders) that are operated by compressed air, hydraulically or electrically, and are designed to move the lower jointed parts of the apparatus in accordance with the human gait and on command of a programmed electronic unit that is in turn operated by the patient by means of a remote control. This permits the patient to transmit to the electronic commands for starting and stopping the lower joints parts of the apparatus or to adjust the step speed.

Figure 1:
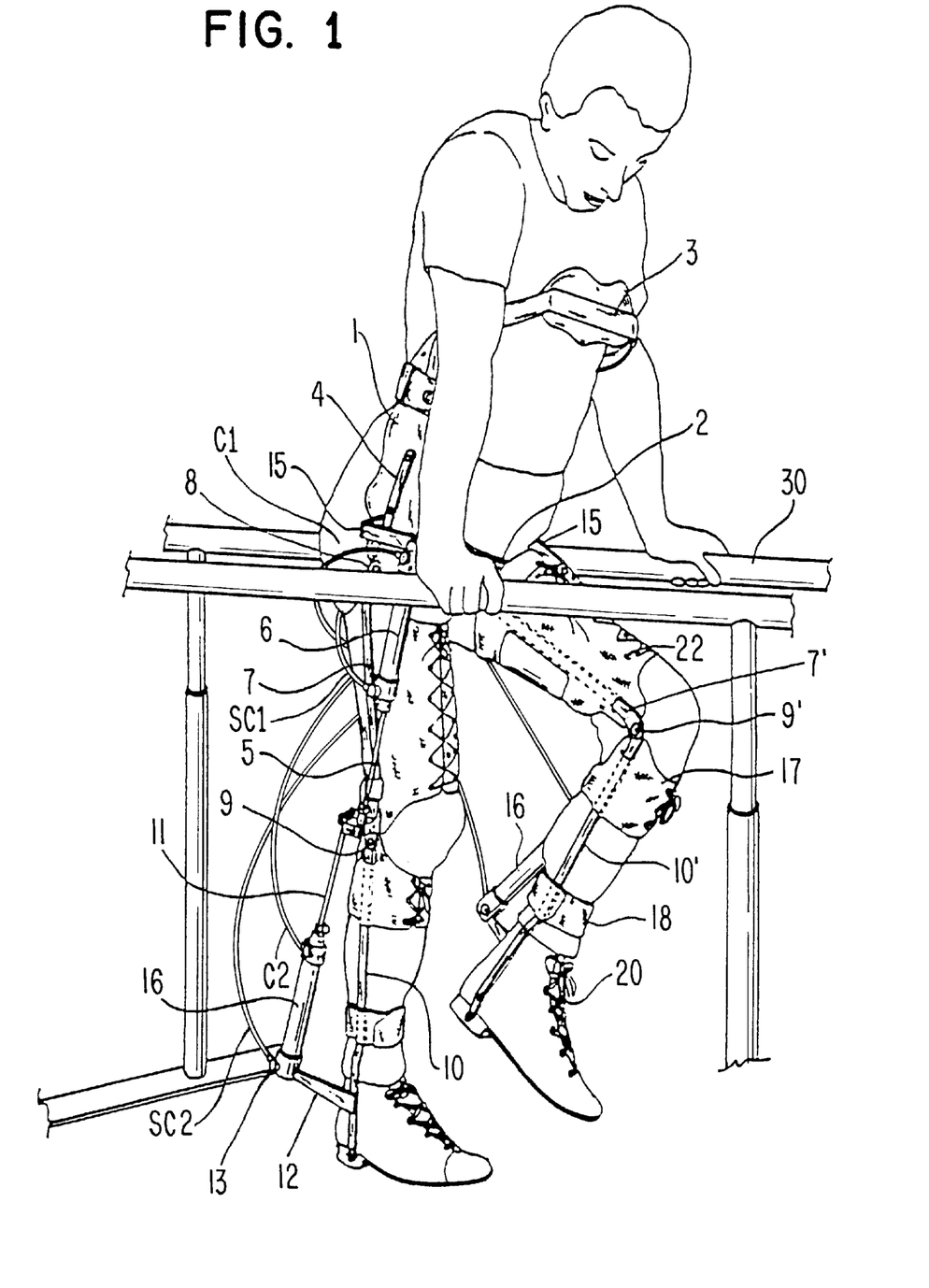
FIG. 1 illustrates a person using a walking apparatus of a known type.

FIG. 1 illustrates a disabled person who is leaning with his hands on two fixed bars. The person is equipped with a walking apparatus of the type which was described above and is disclosed in Italian patent No. 1,178,548. This apparatus comprises a metal corset 1 that is attached to the chest and the pelvis by two attachment devices 2 and 3. On two sides of the corset are fixed metal rods 4 that each have an integral extension 15. At the lower end of the rod 4, at a hinge point A, there is attached a rod 7. The rod 7 extends along the external side of the thigh. A corresponding rod 7' is arranged parallel on the internal side of the thigh, and together with the rod 7 forms a framework of the thigh. A cylinder 6 operated by compressed air or hydraulically is hingedly connected to an end of the extension 15 at an upper end thereof. The cylinder 6 has a rod 5 having a lower end that is connected through a joint to a lower end of the rod 7.

The rod 7 has a lower end that terminates at a hinge 9 that connects the rod 7 with a lower rod 10. The lower rod 10 is part of the leg framework. On the lower part of the rod 10 there is fixed an integral extension 12. The extension 12 is shown enlarged in the drawing in order to provide greater clarity.

A cylinder 16 is connected and hinged to an end of the extension 12, and has a rod 11 that is connected through a joint to a small bracket that is fixed to the lower end of the rod 7. There is a corresponding rod 10' similarly hinged together with the rod 7' for the inner side of the leg.

A plurality of laced bands 17, 18 and 22 allow the rods 7 and 7' and 10 and 10' to be tightened to the thighs and legs of the patient. Extension and retraction of the rod 5 of the cylinder 6 causes relative movement between the thigh and the pelvis. Extension and retraction of the rod 11 causes relative movement between the thigh and the lower leg. The cylinders 6 and 16, which are microcylinders, are operated by tubes C1, C2, SC1 and SC2, which provide for the inlet and outlet of a working fluid such as compressed air or hydraulic fluid. The patient wears on his back a pack (not illustrated) in which are housed compressed air bottles, for example, for operating the cylinders.

Solenoid valves are provided for operating the microcylinders. They are controlled by an electronically or hydraulically operated control unit that is fixed to the patient's belt, and appropriately programmed in order to move the lower jointed parts of the device in accordance with the human gait. The control unit is in turn controlled by means of a manually operated remote control which is located on the patient's corset or belt, and that permits the patient to transmit to the control unit commands for starting or stopping the movement of the lower parts or for adjusting the step speed.

SUMMARY OF THE INVENTION

The object according to the present invention is to further improve the apparatus of the prior art, and more particularly, to further strengthen the stimulation of the recovery of motor abilities and to facilitate the use of an exoskeleton by a patient.

The object according to the present invention is achieved by the provision of an orthopedic apparatus that has an exoskeleton that is adapted to support a user's body, and comprises a plurality of jointed members that are jointed together at articulation positions that correspond to knee and hip joints of the user. Actuators are connected to the jointed members for moving the jointed members relative to each other in a movement corresponding to the human gait. The movements of the human gait are impressed on the user thereby.

A program control unit is connected to the actuators for controlling the operation of the actuators to move in accordance with the human gait. A remote control unit controls the program control unit with start, stop and speed commands for stopping, starting and controlling the speed of the human gait that is impressed on the user by the exoskeleton. The remote control unit has push buttons for the operation thereof.

An electronic virtual reality unit is connected to a virtual reality helmet for wear by the user of the exoskeleton in order to transmit to the user virtual reality pictures and stimulation that is interactive with the human gait that is impressed on the user by the exoskeleton. A framework steadies and supports the user when the exoskeleton impresses the human gait on the user, the framework having grips for the user. Preferably the push buttons are mounted on the grips.

A conveyor belt, according to one embodiment, may support the user during the impression of the human gait upon the user by the exoskeleton. The conveyor belt has a support frame, and the framework is fixed to the support frame. The program control unit is connected with the conveyor belt for control of the conveyor belt thereby, such that the speed of the conveyor belt corresponds to the speed of the human gait that is impressed by the exoskeleton on the user.

In another embodiment, a guide rail is fixed to the floor, and a slide that is slidable along the guide rail is fixed to the framework. The framework comprises four legs, two of the four legs being front legs that have wheels thereon, such that the framework defines a walker for the user that can move across the floor. Two of the four legs are side legs that are fixed to the slide so as to restrict movement of the walker along the guide rail.

The actuators comprise fluid cylinders connected to a source of pressurized fluid, preferably. The source of pressurized fluid and the virtual reality unit can be mounted on the framework.

The exoskeleton generally includes the jointed members being connected to a plurality of bands that are capable of being connected to the user. The program control unit is preferably mounted on one of the bands.

The actuators are relatively small, and are considered to be microcylinders. They can be operated by compressed air, hydraulically or electrically.

A further object according to the present invention is to further improve the apparatus of the prior art, and more particularly, to strengthen the stimulation of the recovery of motor abilities in tetraplegic patients, and to facilitate and stimulate the revival of comatose patients.

This further object is achieved by an orthopedic apparatus comprising an exoskeleton adapted to support a user's body, articulated at articulation positions of the user's body and provided with small actuators ("microcylinders") operated by compressed air, hydraulically or electrically, designed to move the articulated parts of the exoskeleton in accordance with the human gait. A programmed control unit controls the operation of the actuators to move the exoskeleton in accordance with the human gait. A remote control unit controls the programmed control unit with commands for stopping, starting or controlling the speed of the human gait. An electronic virtual reality unit transmits to the user, by means of a virtual reality helmet, suitable virtual reality pictures and stimulation interactive with the human gait that is impressed on the user by the exoskeleton. A rail suspended at a distance from the ground higher than human height supports and guides a ball bearing or a slide slidable inside or on the rail. A metal framework is supported by the ball bearing or slide and provided with two suspenders or rods for supporting the exoskeleton of the patient.

BRIEF DESCRIPTION OF THE DRAWINGS

Further objects, features and advantages of the present invention will be apparent from the following detailed description taken in conjunction with the accompanying drawings, in which.

DETAILED DESCRIPTION OF THE PREFERRED EMBODIMENTS

Figure 2:
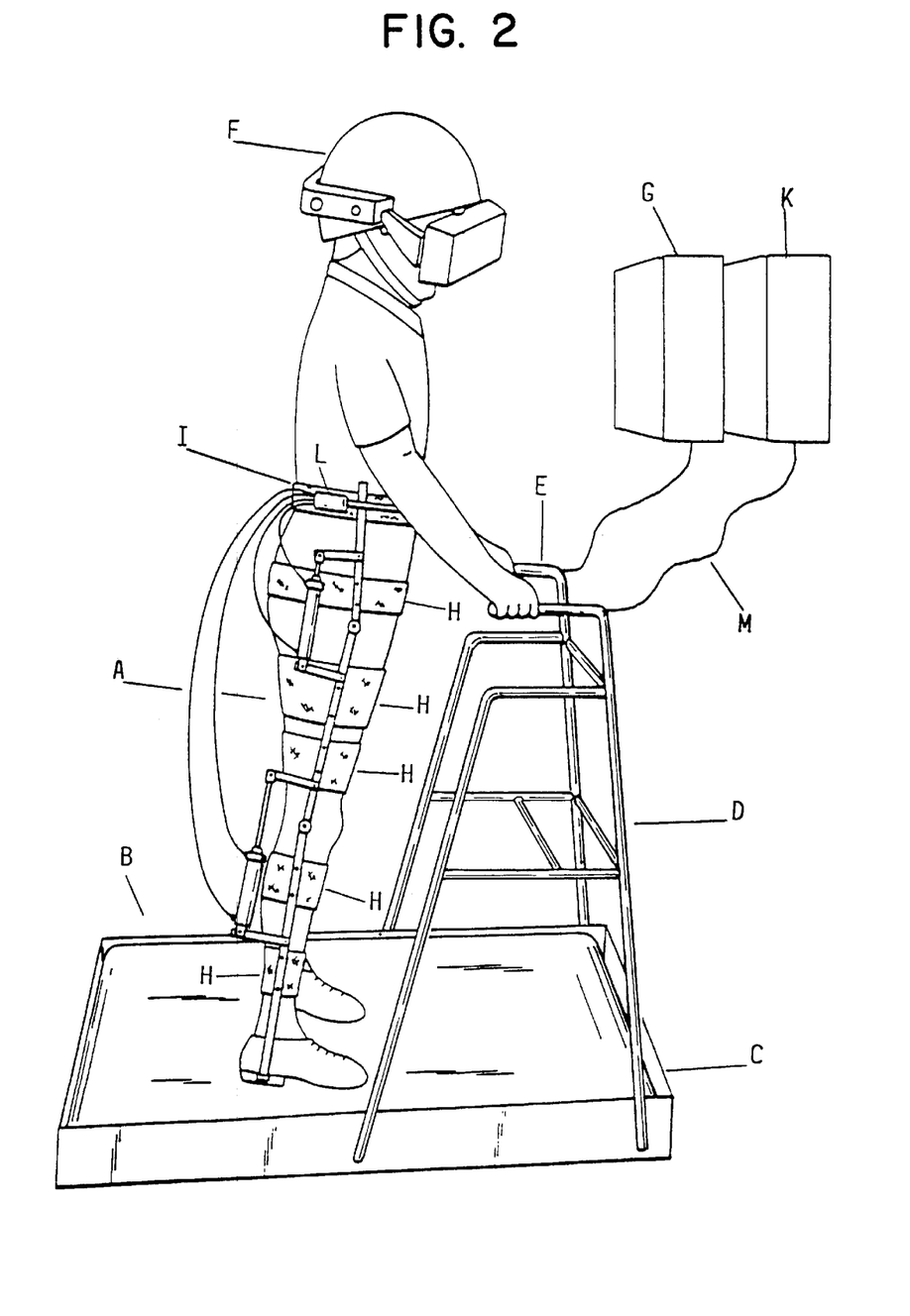
FIG. 2 illustrates a first example of a walking and rehabilitating apparatus according to the present invention.

FIG. 2 illustrates a disabled person employing a rehabilitation apparatus in accordance with a first embodiment of the present invention. This apparatus has a sling or exoskeleton A that is laced to the person or patient's body. The sling is similar to that illustrated in FIG. 1, but is improved over the sling of FIG. 1 as will be explained below.

A conveyor belt B provides a support for the patient's feet, and has a rectangular frame C that surrounds the belt and supports rollers of the conveyor belt B. A tubular framework D is fixed to the rectangular frame C, and is designed to act mainly as a support for the patient through two upper grips E.

A helmet F is worn by the patient, and is provided with earphones and viewers that are connected to an electronic virtual reality unit G.

The sling or exoskeleton that is shown in FIG. 2 is improved with respect to that of FIG. 1 by making the frame members that were previously metallic parts out of an ultralight material such as a carbon fiber and titanium. This reduces the weight on the patient's body in movement and permits an independent wearing of the exoskeleton or sling by the patient, in contrast to the sling or exoskeleton of FIG. 1. Such independent wear of the sling or exoskeleton is further facilitated by the use of bands H employing hook and loop type fasteners such as Velcro™. It is further improved by, for patients who are capable of holding their chest erect, a corset that is essentially limited to a belt I.

The control unit (not shown), in addition to controlling the operation of the solenoid valves, which are enclosed in a distribution box L provided on a belt I, controls movement of the conveyor belt. It is programmed to regulate the running speed of the conveyor belt in dependence upon the speed of the walking movement of the exoskeleton.

Instead of being placed on the patient's belt, the remote control operating push buttons are, with this embodiment, located on the hand grips E of the tubular frame D. This allows the patient to timely operate the remote control during any phase of walking. The precise positioning of the operating push buttons is not illustrated in the figures.

Furthermore, a source of pressurized fluid, such as compressed air bottles, are no longer located on the patient's back. This is because they can be located in a special delivery unit K having a delivery duct M. The duct M is appropriately connected to the framework, for example, and can have a passage extending through the framework, or at least an anchoring point on the framework D.

As an alternative, the source of pressurized fluid, or delivery means, could be located on the framework D itself, comprising either a simple compressed gas (for example air) bottle, or a compressor, or a pump that provides hydraulic operation of the microcylinders.

The special delivery unit K and its delivery duct M, whatever its configuration, of course has a fluid passage or connection to the distribution box L for operation of the microcylinders.

The cable that connects the electronic virtual reality unit G to the patient's helmet can also pass through the framework E, or at least have an appropriate anchor point on the framework D. The virtual reality unit G is programmed to transmit to the patient virtual reality pictures and stimulation that is interactive with the walking movement that is impressed by the exoskeleton on the patient's body. This involves the patient emotionally, which is important, because therapeutic efficacy is proportional to the emotional involvement of the patient.

Examples of the types of virtual reality pictures and stimulation are pictures and stimulation that are related to the path which, according to the pictures projected in the helmet, the patient believes he is following, and can reflect situations of emergency and danger that occur along the path, or pictures and stimulation that are related to paths that are particularly dear or at least significant in the memory of the patient. Sounds and voices that can be either danger signals, or sounds, music and voices that are particularly dear to the patient, can also be provided.

In order to explain the utility of the equipment in accordance with the present invention, and in particular the use of virtual reality with the present invention, the following observations are pertinent. It is known that lesions or amputations of the spinal medulla due to injuries to the spinal column, inflammation of the medulla or the vertebra, tumors or serious vascular disorders can cause paralysis of the lower limbs due to the fact that the lesions constitute a break in the transmission of nervous motor impulses from the brain. It is also known that the motor program of the limbs is not located only in the brain, but also in the spinal medulla, as proven by the fact that animals run on their own legs for a few moments even after amputation of the head.

The above observations serve as a key for the interpretation of rehabilitation methods that are based on a program of exercise for the patient in walking in a manner as natural as possible with the aid of special support and motor mechanisms for the legs. These methods allow not only the reactivation or rememorization of the motor program of the legs in the spinal medulla, but also progressively reactivate the passage of the nervous impulses from the brain in the injured zone of the medulla. The usefulness of virtual reality in this situation is based on the properties of adrenaline and noradrenaline and on the fact that the secretion of adrenaline is stimulated upon the occurrence of emergency situations such as strenuous efforts, emotions, danger signals, arterial hypotension, asphyxia, hypothermia, etc. The growth of the concentration of adrenaline in the blood can be up to levels that are 300 times normal. The adrenaline and noradrenaline hormones have the function of preparing the system both physically and emotionally to face emergency situations. Among their various effects is a stimulation of the nervous system. In particular, adrenaline and noradrenaline act as neurotransmitters. That is, they are chemical intermediaries that allow the transmission of nervous impulses from one neuron to another.

It is thus understandable how useful virtual reality could be during a patient's walking exercises as a means of stimulating the transmission of nervous impulses in the injured zone of the medulla through virtual reality pictures, sensations and emotions that are designed to stimulate the increase of the adrenaline levels in the blood.

It could be advantageous to use the apparatus according to the present invention without the use of the virtual reality helmet, either before starting therapy with the helmet, in order to allow the patient to gain familiarity and practice in the use of the conveyor belt, or after the therapy cycle with the helmet, when the voluntary mobility of the lower limbs has begun to appear.

Figure 3:
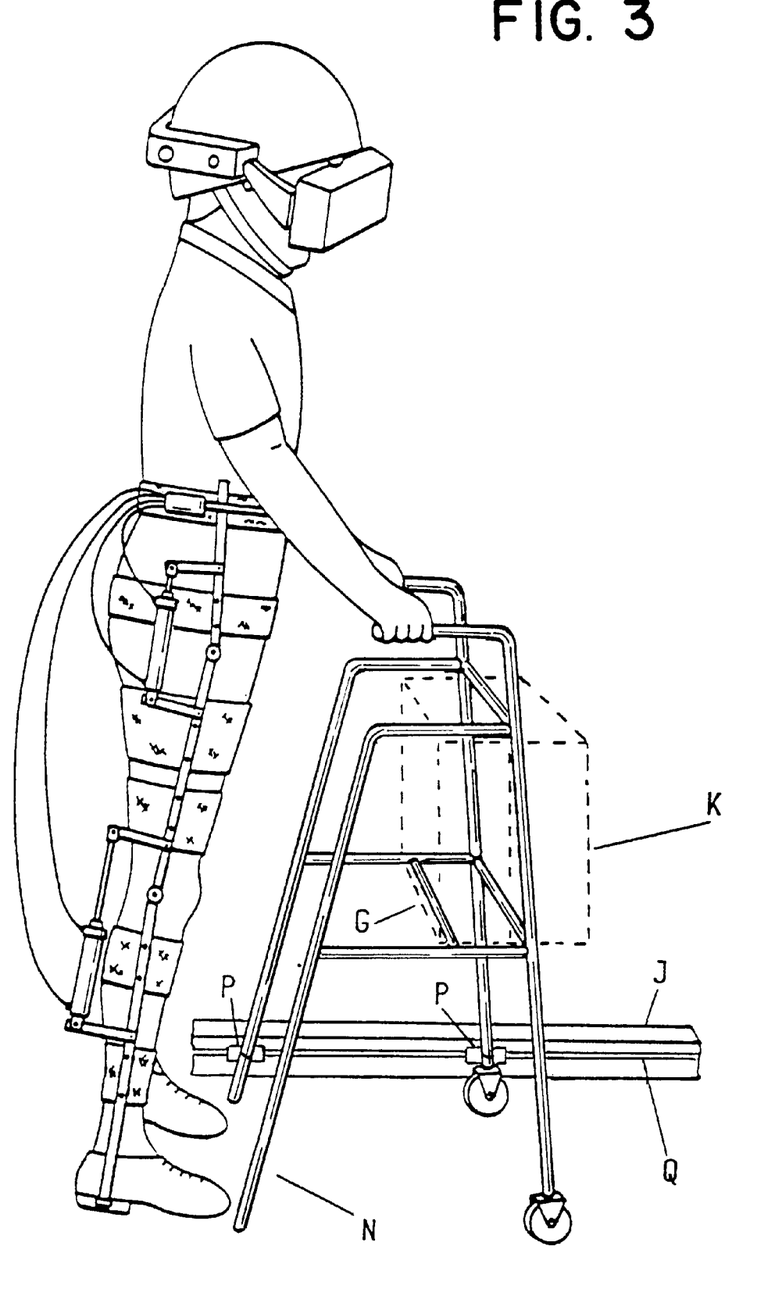
FIG. 3 illustrates a second embodiment in accordance with the present invention.

FIG. 3 is an illustration of a disabled person using a rehabilitation apparatus according to a second embodiment of the present invention. The main difference between the example of FIG. 3 and that of FIG. 2 is the lack of the conveyor belt, and the conversion of the tubular frame into a four legged hand walker N with the front legs thereof being fitted with wheels. With this type of arrangement, the patient can move around in the room.

In order to facilitate the walking of the patient, it may be appropriate to install in the room where the walking exercises take place a rail J that is equipped with slides P running along a groove Q in the rail. The slides P are firmly fixed through rings, for example, to the two legs of the hand walker that are on one side thereof, so that the walking of the patient is guided. The constraint of the use of the walker along the rail can be removed as soon as the rehabilitation has progressed to the point where use of the virtual reality helmet is no longer required. The electronic virtual reality unit G and the pressurized fluid delivery unit K can still be located in fixed positions, as shown in FIG. 2, or they could be installed in the frame N, as shown in broken lines in FIG. 3.

Figure 4A:
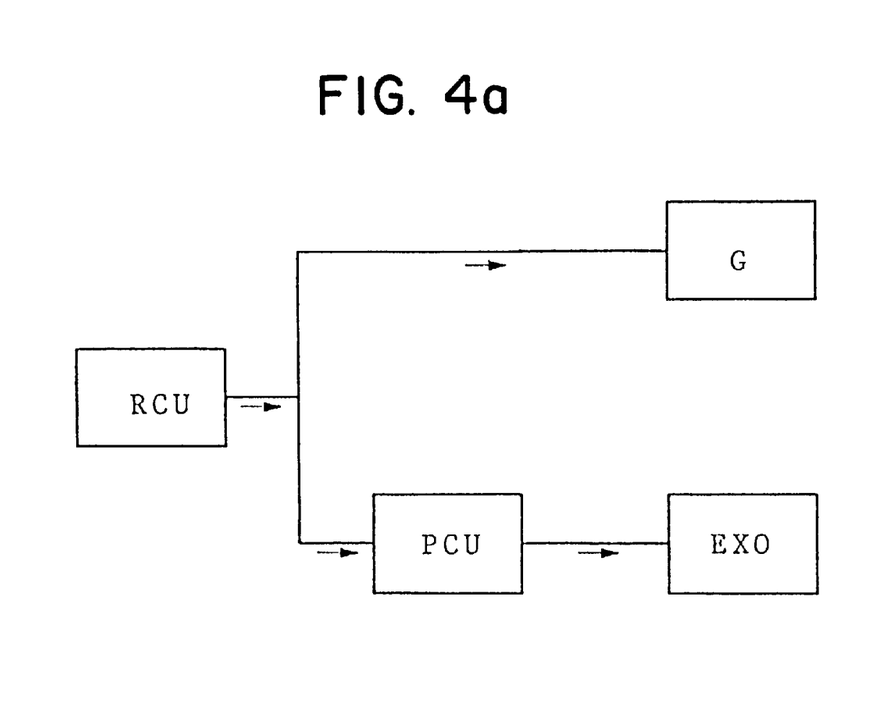
FIGS. 4(a) and 4(b) are schematic illustrations of the relationship between control units, a virtual reality unit and a walking apparatus.
Figure 4B:
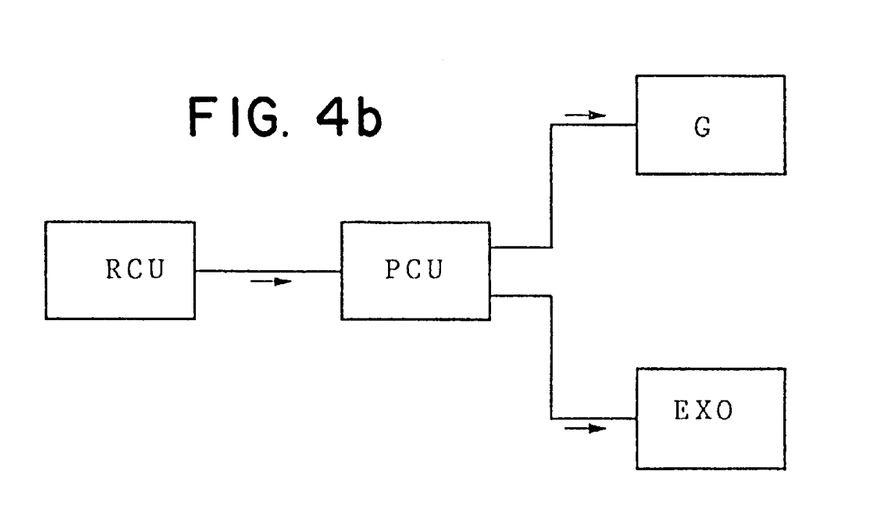

FIGS. 4a and 4b illustrate two different arrangements of the control system for the above-described embodiments of the present invention. It should also be noted that these same arrangements could also apply to the embodiment described with respect to FIG. 5.

In the Figures, RCU refers to the remote control unit, PCU refers to a programmed control unit, G refers to the virtual reality unit, and EXO refers to the exoskeleton. The remote control unit in FIG. 4a sends instructions to both the program control unit and the virtual unit. Thus, the program control unit, under the control of the remote control unit, controls the exoskeleton. The virtual reality unit is controlled directly by the remote control unit. Alternatively, in FIG. 4b, the remote control unit controls only the program control unit, which subsequently controls both the virtual reality unit and the exoskeleton.

With the control system as described, pictures transmitted by the virtually reality unit G to the patient, such as images of a road or path through a field, are dependent upon the movement of the exoskeleton, so that accelerations of the gait, or stops, cause congruent changes of the picture that is transmitted by the virtual reality unit. Thus in suitably controlling the exoskeleton with the remote control unit, the virtual reality unit is also controlled to show the appropriate image corresponding to the movement, and they are coordinated.

It should be noted that paraplegics show signs of insecurity when they are using an exoskeleton, due to their loss of natural motor ability and their ability to maintain their balance. Thus the idea of adding a virtual unit to the use of an exoskeleton does not initially appear to be a good idea, because it might be judged to increase the sense of insecurity by the patient, and the sense of loss of balance due to the fact that the patient can not see the real environment that the patient is moving in. However, use of the virtual reality device has shown that initial expectations of greater insecurity and a greater sense of loss of balance by patients does not occur.

Figure 5:
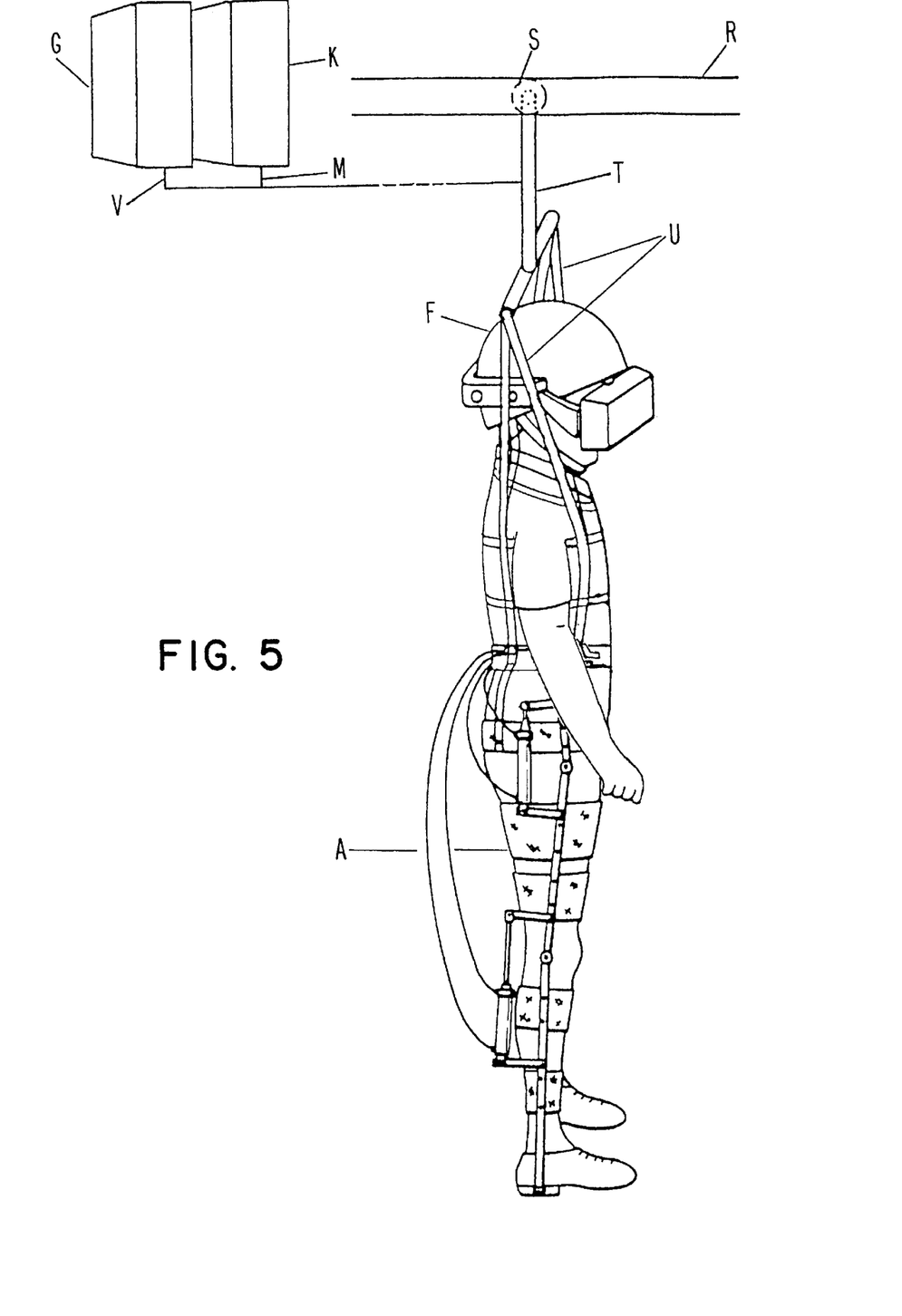
FIG. 5 illustrates a further example of an apparatus according to the present invention.

FIG. 5 illustrates a disabled person employing a rehabilitation apparatus in accordance with another embodiment of the present invention. This apparatus comprises a sling (exoskeleton) A laced to patient's body, similar to that illustrated in FIG. 1, but improved over the sling of FIG. 1 as will be explained below. A rail R is suspended at a distance from the ground higher than human height, for supporting and guiding a ball bearing or a slide S slidable inside or on the rail. A metal framework T is supported by the ball bearing or slide S and provided with two suspenders or rods U for supporting the sling of the patient. A helmet F worn by the patient is provided with earphones and viewers that are connected to an electronic virtual reality unit G. The exoskeleton that is shown in FIG. 2 is improved with respect to that of FIG. 1 by making the frame members that were previously metallic parts out of an ultralight material such as a carbon fiber and titanium, in order to reduce the weight on the patient's body in movement.

Moreover, the sling is extended on the upper part in order to support the patient's bust and, in case, even his head or the helmet F. The rail R extends over a circular route, but could cover a rectilinear route. In the last case, a device should be provided which might cause the framework to revolve 180 degrees at the end of the run so that the patient, with the help of a hospital attendant, might revolve and begin a new run in the opposite direction.

The remote control unit for controlling the programmed control unit which controls the operation of the exoskeleton actuators shall always be in the hands of a hospital attendant in order to ensure a timely operation of the same during any phase of the walking with this embodiment.

The means of supplying pressurized fluid can be located in a special delivery unit K whose delivering duct M can have a passage extending through the framework T, or at least an anchoring point on the same framework. The supplying means can be either a simple compressed gas (for example air) bottle, or a compressor, or a pump that provides hydraulic operation of the microcylinders.

The special delivery unit K and its delivery duct M, whatever its configuration, of course has a fluid passage or connection to the distribution box L for operation of the microcylinders.

Even cable V that connects the electronic virtual reality unit G to the patient's helmet can pass through the framework T, or at least have an appropriate anchor point on the same. The virtual reality unit G is programmed to transmit to the patient virtual reality pictures and stimulation that is interactive with the walking movement that is impressed by the exoskeleton on the patient's body. This involves the patient emotionally, which is important, because therapeutic efficacy is proportional to the emotional involvement of the patient. Note the above discussion.

The voices, sounds and pictures transmitted by the virtual reality helmet prove very helpful in facilitating and stimulating the revival of comatose patients. It could be advantageous to use the apparatus according to the present invention without the use of the virtual reality helmet, either before starting therapy with the helmet, in order to allow the patient to gain familiarity and practice in the use of the conveyor belt, or after the therapy cycle with the helmet, when the voluntary mobility of the lower limbs has begun to appear.

It will be clear to those of skill in the art that numerous modifications, adaptations, variations and substitutions of various elements through other elements can be made to the above-described embodiments and should be considered within the scope of the present invention. For example, the two slides P that are illustrated in FIG. 3 could be replaced by a single slide that is fixed to one side of the frame N.

I claim:

1. An orthopedic apparatus comprising:
    an exoskeleton to be attached to a person for active movement of limbs of the person and emulation of human gait;
    a programmed control unit operably connected to said exoskeleton, operable to control said exoskeleton so as to move said exoskeleton in a movement corresponding to a human gait;
    a virtual reality unit to be worn by the person, operable to transmit information to the person so as to generate a virtual environment;
    a remote control unit operably connected to said virtual reality unit and said programmed control unit, operable to control both a movement of said exoskeleton via said programmed control unit and said virtual reality unit such that the virtual environment generated by said virtual reality unit corresponds to the movement of said exoskeleton controlled by said remote control so that the movement of said exoskeleton and the virtual environment generated by said virtual reality unit are coordinated.

2. An orthopedic apparatus as claimed in claim 1, wherein said remote control unit is operable to control and coordinate a speed of the movement of said exoskeleton via said programmed control unit and a speed of the virtual environment generated by said virtual reality unit.

3. An orthopedic apparatus as claimed in claim 1, wherein said remote control unit is operable to control and coordinate a starting of the movement of said exoskeleton via said programmed control unit and a starting of the virtual environment generated by said virtual reality unit.

4. An orthopedic apparatus as claimed in claim 1, wherein said remote control unit is operable to control and coordinate a stopping of the movement of said exoskeleton via said programmed control unit and a stopping of the virtual environment generated by said virtual reality unit.

5. An orthopedic apparatus as claimed in claim 1, wherein said remote control unit includes push buttons operable to receive control instructions from the person, and said remote control unit is operable to control both the movement of said exoskeleton and the virtual environment based on the control instructions received by said push buttons.

6. An orthopedic apparatus as claimed in claim 1, wherein said exoskeleton is to be attached to legs of the person, and said programmed control unit is operable to control said exoskeleton in a movement corresponding to a gait of human legs.

7. An orthopedic apparatus as claimed in claim 1, wherein said virtual reality unit includes a virtual reality helmet, to be worn by the person, operable to transmit the information to the person so as to generate the virtual environment.

8. An orthopedic apparatus as claimed in claim 1, further comprising a framework, including grips, operable to steady the person during the movement of said exoskeleton.

9. An orthopedic apparatus as claimed in claim 8, wherein said remote control unit includes push buttons, mounted on said grips, operable to receive control instructions from the person, and said remote control unit is operable to control both the movement of said exoskeleton and the virtual environment based on the control instructions received by said push buttons.

10. An orthopedic apparatus as claimed in claim 8, further comprising:
    a conveyor belt operable to support the person during the movement of said exoskeleton, said conveyor belt having a support frame;
    wherein said framework is fixed to said support frame and said programmed control unit is connected with said conveyor belt for controlling said conveyor belt such that a speed of said conveyor belt corresponds to a speed of the movement of said exoskeleton.

11. An orthopedic apparatus as claimed in claim 8, further comprising a source of pressurized fluid for operating said exoskeleton, wherein said source of pressurized fluid and said virtual reality unit are mounted on said framework.

12. An orthopedic apparatus as claimed in claim 9, further comprising:
   a rail;
   a slide member in contact with said rail such that said slide member is capable of sliding along said rail;
   a framework, supported by said slide member, connected to said exoskeleton such that said slide member supports said framework and said exoskeleton from said rail.

13. An orthopedic apparatus as claimed in claim 12, wherein said slide member includes a ball bearing.

14. An orthopedic apparatus as claimed in claim 12, wherein said rail extends over a circular route.

15. An orthopedic apparatus as claimed in claim 12, wherein said rail extends over a rectilinear route and comprises a device which causes said framework to revolve 180 degrees at an end of the route so that the person can revolve and begin anew in an opposite direction.

16. An orthopedic apparatus as claimed in claim 1, further comprising:
   a guide rail;
   a slide member in contact with said guide rail such that said slide member is capable of sliding along said guide rail;
   a walker framework including legs, wherein at least one of said legs includes a wheel, and at least one of said legs is fixed to said slide member so as to restrict movement of said walker framework along said guide rail.

17. An orthopedic apparatus as claimed in claim 1, wherein said exoskeleton includes jointed members connected to a plurality of bands that are capable of being connected to the person, and said programmed control unit is mounted to at least one of said bands.

18. An orthopedic apparatus comprising:
   an exoskeleton to be attached to a person for active movement of limbs of the person and emulation of human gait;
   a virtual reality unit to be worn by the person, operable to transmit information to the person so as to generate a virtual environment;
   a programmed control unit operably connected to said exoskeleton and said virtual reality unit, operable to control said exoskeleton so as to move said exoskeleton in a movement corresponding to a human gait and to control said virtual reality unit;
   a remote control unit operably connected to said programmed control unit, operable to control both a movement of said exoskeleton and said virtual reality unit via said programmed control unit such that the virtual environment generated by said virtual reality unit corresponds to the movement of said exoskeleton controlled by said remote control so that the movement of said exoskeleton and the virtual environment generated by said virtual reality unit are coordinated.

19. An orthopedic apparatus as claimed in claim 18, wherein said remote control unit is operable to control and coordinate a speed of the movement of said exoskeleton and a speed of the virtual environment generated by said virtual reality unit via said programmed control unit.

20. An orthopedic apparatus as claimed in claim 18, wherein said remote control unit is operable to control and coordinate a starting of the movement of said exoskeleton and a starting of the virtual environment generated by said virtual reality unit via said programmed control unit.

21. An orthopedic apparatus as claimed in claim 18, wherein said remote control unit is operable to control and coordinate a stopping of the movement of said exoskeleton and a stopping of the virtual environment generated by said virtual reality unit via said programmed control unit.

22. An orthopedic apparatus as claimed in claim 18, wherein said remote control unit includes push buttons operable to receive control instructions from the person, and said remote control unit is operable to control both the movement of said exoskeleton and the virtual environment based on the control instructions received by said push buttons.

23. An orthopedic apparatus as claimed in claim 18, wherein said exoskeleton is to be attached to legs of the person, and said programmed control unit is operable to control said exoskeleton in a movement corresponding to a gait of human legs.

24. An orthopedic apparatus as claimed in claim 18, wherein said virtual reality unit includes a virtual reality helmet, to be worn by the person, operable to transmit the information to the person so as to generate the virtual environment.

25. An orthopedic apparatus as claimed in claim 18, further comprising a framework, including grips, operable to steady the person during the movement of said exoskeleton.

26. An orthopedic apparatus as claimed in claim 25, wherein said remote control unit includes push buttons, mounted on said grips, operable to receive control instructions from the person, and said remote control unit is operable to control both the movement of said exoskeleton and the virtual environment based on the control instructions received by said push buttons.

27. An orthopedic apparatus as claimed in claim 25, further comprising:
   a conveyor belt operable to support the person during the movement of said exoskeleton, said conveyor belt having a support frame;
   wherein said framework is fixed to said support frame and said programmed control unit is connected with said conveyor belt for controlling said conveyor belt such that a speed of said conveyor belt corresponds to a speed of the movement of said exoskeleton.

28. An orthopedic apparatus as claimed in claim 25, further comprising a source of pressurized fluid for operating said exoskeleton, wherein said source of pressurized fluid and said virtual reality unit are mounted on said framework.

29. An orthopedic apparatus as claimed in claim 18, further comprising:
   a rail;
   a slide member in contact with said rail such that said slide member is capable of sliding along said rail;
   a framework, supported by said slide member, connected to said exoskeleton such that said slide member supports said framework and said exoskeleton from said rail.

30. An orthopedic apparatus as claimed in claim 29, wherein said slide member includes a ball bearing.

31. An orthopedic apparatus as claimed in claim 29, wherein said rail extends over a circular route.

32. An orthopedic apparatus as claimed in claim 29, wherein said rail extends over a rectilinear route and comprises a device which causes said framework to revolve 180 degrees at an end of the route so that the person can revolve and begin anew in an opposite direction.

33. An orthopedic apparatus as claimed in claim 15, further comprising:
- a guide rail;
- a slide member in contact with said guide rail such that said slide member is capable of sliding along said guide rail;
- a walker framework including legs, wherein at least one of said legs includes a wheel, and at least one of said legs is fixed to said slide member so as to restrict movement of said walker framework along said guide rail.

34. An orthopedic apparatus as claimed in claim 18, wherein said exoskeleton includes jointed members connected to a plurality of bands that are capable of being connected to the person, and said programmed control unit is mounted to at least one of said bands.

35. A method for rehabilitating motor abilities of a patient for use with an exoskeleton controlled by a programmed control unit so as to have a movement corresponding to a human gait, a virtual reality unit, and a remote control unit, said method comprising:
- attaching the exoskeleton to the patient;
- fitting the virtual reality unit to the patient;
- transmitting information to the patient with the virtual reality unit so as to generate a virtual environment for the patient; and
- controlling both the movement of the exoskeleton corresponding to the human gait and the virtual reality unit with the remote control such that the virtual environment generated by the virtual reality unit corresponds to the movement of the exoskeleton controlled by the remote control so that the movement of the exoskeleton and the virtual environment generated by the virtual reality unit are coordinated.

36. A method as claimed in claim 35, comprising:
- controlling and coordinating a speed of the movement of the exoskeleton and a speed of the virtual environment generated by the virtual reality unit with the remote control.

37. A method as claimed in claim 35, comprising:
- controlling and coordinating a starting of the movement of the exoskeleton and a starting of the virtual environment generated by the virtual reality unit with the remote control.

38. A method as claimed in claim 35, comprising:
- controlling and coordinating a stopping of the movement of the exoskeleton and a stopping of the virtual environment generated by the virtual reality unit with the remote control.

39. A method as claimed in claim 35, comprising:
- attaching the exoskeleton to legs of the patient; and
- controlling the exoskeleton in a movement corresponding to a gait of human legs with the remote control.

40. A method as claimed in claim 35, for further use with a virtual reality helmet, said method comprising:
- fitting the virtual reality helmet to the patient; and
- transmitting the information to the patient via the virtual reality helmet so as to generate the virtual environment.

41. A method as claimed in claim 35, for further use with a framework, said method comprising:
- steadying the patient with the framework during the movement of the exoskeleton.

* * * * *